United States Patent [19]
Kalchauer et al.

[11] Patent Number: 5,336,799
[45] Date of Patent: Aug. 9, 1994

[54] PROCESS FOR THE REMOVAL OF HYDROGEN-CONTAINING SILANES FROM METHYLCHLOROSILANES

[75] Inventors: Wilfried Kalchauer; Bernd Pachaly, both of Burghausen, Fed. Rep. of Germany

[73] Assignee: Wacker-Chemie GmbH, Munich, Fed. Rep. of Germany

[21] Appl. No.: 143,591

[22] Filed: Nov. 1, 1993

[30] Foreign Application Priority Data

Dec. 3, 1992 [DE] Fed. Rep. of Germany ....... 4240717

[51] Int. Cl.$^5$ ............................................... C07F 7/08
[52] U.S. Cl. ..................................................... 556/466
[58] Field of Search ......................................... 556/466

[56] References Cited

U.S. PATENT DOCUMENTS

| | | | |
|---|---|---|---|
| 2,594,946 | 4/1952 | Lucas | 556/466 |
| 3,704,260 | 11/1972 | Wynn | 556/466 |
| 4,156,689 | 5/1979 | Ashby et al. | 556/466 |
| 4,297,500 | 10/1981 | Finke et al. | 556/466 |
| 4,774,347 | 9/1988 | Marko et al. | 556/462 |
| 4,985,579 | 1/1991 | Bokerman et al. | 556/466 |
| 5,138,081 | 8/1992 | DeVries et al. | 556/466 |

FOREIGN PATENT DOCUMENTS 0423948  4/1991  European Pat. Off. .

OTHER PUBLICATIONS

W. Noll, Chemistry and Technology of Silicones, Academic Press, Inc. Orlando, Fla., 1968, Chapter 2.2.
D. J. Citron, J. E. Lyons; L. H. Sommer (The Journal of Organic Chemistry), 1969, vol. 34, p. 638.
A. Hunyar, Chemie D. Silikone, Verlag Technik Berlin 1952, pp. 92–94.

*Primary Examiner*—Paul F. Shaver
*Attorney, Agent, or Firm*—Martin Connaughton

[57] ABSTRACT

Silanes containing hydrogen atoms bonded directly to silicon produced as by-products during methylchlorosilane synthesis are reacted with chlorohydrocarbons in the presence of palladium or platinum as catalysts to give the corresponding chlorosilanes.

6 Claims, No Drawings

PROCESS FOR THE REMOVAL OF HYDROGEN-CONTAINING SILANES FROM METHYLCHLOROSILANES

FIELD OF INVENTION

The invention relates to a process for the removal of silanes containing hydrogen atoms bonded directly to silicon from the product mixtures obtained during methylchlorosilane synthesis.

BACKGROUND OF INVENTION

The direct synthesis of methylchlorosilanes is carried out by reacting silicon and methyl chloride at 250° to 300° C. in the presence of copper catalysts. In addition to the silanes of the general formula $Me_xSiCl_{4-x}$, in which x has a value from 0 to 4 and Me here and below denotes a methyl group, small amounts of ethylchlorosilanes, various hydrodosilanes, above all $Me_yH$-$SiCl_{3-y}$, in which y has a value from 0 to 2, and ethyldichlorosilane $EtHSiCl_2$ are also formed. Various straight- and branched-chain alkanes, alkenes and chlorohydrocarbons having up to 9 carbon atoms appear as impurities. The direct synthesis is described, inter alia, in W. Noll, Chemistry and Technology of Silicones, Academic Press, Inc., Orlando, Fla., 1968, chapter 2.2.

The most sought-after target product of the direct synthesis is $Me_2SiCl_2$, which can be converted by hydrolysis and polycondensation into silicone polymers having diverse functional groups and structures.

An essential quality feature of most silicone polymers is as low a content as possible of trifunctional impurities in the polymer skeleton. One of the possible trifunctional impurities of the $Me_2SiCl_2$ employed is $EtHSiCl_2$.

Since the boiling points of $Me_2SiCl_2$ (70°–71° C.) and $EtHSiCl_2$ (74°–76° C.) differ from one another by only about 4° C., a very distillative effort, such as high reflux ratios, a large number of theoretical plates, and trays in practice, a high energy requirement and a reduced space/time yield, is necessary to obtain the $Me_2SiCl_2$ in the purity required for the particular use.

EP-A 423,948 describes the conversion of hydrogen-containing alkylsilane impurities into the corresponding alkylchlorosilanes using hydrogen chloride gas and suitable catalysts of Pd, Pt, Rh, Ru, Ni, Os, Ir and compounds thereof. The difference in boiling points between the target product and impurity is increased by this measure such that the distillation can be operated with a considerably reduced effort.

The disadvantage of this process is that hydrogen chloride additionally has to be introduced into the silane product stream in an amount of hydrogen chloride above the stoichiometrically required amount must be employed. The excess portions of hydrogen chloride interfere in the subsequent distillation and therefore have to be removed beforehand. Another disadvantage of the process described is that at an original H-silane concentration in the range from 10 ppm to 10%, a contact time of more than 1 minute is preferably for adequate conversion of the hydrogen-containing silane. The reaction of chlorohydrocarbons with halogen-free hydrogen-containing silanes in the presence of noble metal catalysts to form hydrocarbons and chlorosilanes is known, for example, from D. J. Citron, J. E. Lyons; L. H. Sommer, (The Journal of Organic Chemistry, 1969, volume 34, page 638). In this case, the degrees of conversion depend very greatly on the individual components and the catalyst.

U.S. Pat. No. 4,774,347 describes a process for reducing the chlorohydrocarbon content in silane streams in the presence of hydrogencontaining silanes with the aid of catalysts which form Lewis acids. Aluminum, aluminum silicates, zeolites, aluminum chloride, cobalt chloride, iron chloride, copper chloride, tin chloride, palladium chloride or zirconium chloride are employed as catalysts in this process.

The disadvantage of this process is that the halogen-containing catalysts dissolve in the methylchlorosilanes, as a function of the temperature, and that the oxides and metals mentioned are in some cases converted into the corresponding chlorine compounds and thereby into a soluble form. This means that the catalysts mentioned can be employed in a continuous reaction in the liquid phase carried out industrially to only a limited extent, since the catalyst is dissolved off the support material and removed from the reaction system with the methylchlorosilane stream. The service life of the catalyst is thereby greatly reduced. In addition, the silanes are contaminated with metal halides. Another disadvantage of the process is that a contact time of the components on the catalyst of more than one minute is necessary for corresponding degrees of conversion.

SUMMARY OF INVENTION

The object of the present invention is to provide a process for the removal of silanes containing hydrogen atoms bonded directly to silicon (H-silanes) from product mixtures obtained during methylchlorosilane synthesis, in which no hydrogen chloride has to be added, in which the catalyst does not dissolve in methylchlorosilanes or react with these to give the corresponding halogen compounds and in which the rates of reaction are so high that contact times on the catalyst of less than one minute—at adequate degrees of conversion—are possible.

The invention relates to a process for the removal of silanes containing hydrogen atoms bonded directly to silicon from product mixtures obtained during methylchlorosilane synthesis in which the silanes containing hydrogen atoms bonded directly to silicon are reacted with chlorohydrocarbons in the presence of metallic palladium or platinum as catalysts to give the corresponding chlorosilanes.

The H-silanes can be converted by the process according to the invention virtually completely into higher-boiling chlorosilanes in which a chlorine atom is bonded at the point where the hydrogen atom was previously bonded. If these chlorosilanes are undesirable in the product mixture, they can easily be removed by distillation.

Other advantages of the process according to the invention are that the distillation effect, for example for the preparation of pure dimethyldichlorosilane, can be reduced considerably and in this way the space/time yield of the columns can be increased considerably, which means that a saving in energy results. Only short reaction times are required for the process. It is not necessary to maintain a stoichiometric excess of hydrogen chloride and the catalyst is present in a solid form which is insoluble in the methylchlorosilane, that is to say the reaction is catalyzed heterogeneously. This is advantageous in that it allows the use of the catalyst in a distillation reaction column or in a flowthrough reactor and ensures long catalyst service lives.

None of the above referenced publications disclose that the reaction of the H-silanes with chlorohydrocarbons in the presence of metallic platinum catalysts or palladium catalysts can be employed as a suitable method for removal of H-silanes from silane product streams. The reactions as described generally disclose incomplete reaction and/or a relatively slow process. This is unacceptable because even at low concentrations H-silanes need to be removed quickly and completely from the product streams.

In the present invention the catalysts employed are metallic palladium or platinum, palladium being particularly preferred.

The catalyst is preferably employed in finely divided form, in which case it is preferably on supports.

Examples of supports are active charcoal, charcoal and inorganic oxides, such as silicon dioxide, titanium dioxide and zirconium dioxide; carbides, such as silicon carbide; charcoal, active charcoal and silicon dioxide being preferred examples.

Such catalysts in which the finely divided metals are on supports are commercially obtainable, such as, for example, 1% palladium-on-silicon dioxide from Heraeus GmbH, Germany or for example, 3% platinum-on--active charcoal from Johnson Matthey GmbH, Germany.

The concentrations of the metals on the supports are preferably 0.8 to 10% by weight, based on the total weight of the catalyst, such as are usually present on the commercially obtainable products; however, it is also possible to use higher or lower concentrations.

The process according to the invention is particularly suitable for the purification of dimethyldichlorosilane which, as a result of the direct synthesis, contains EtHSiCl$_2$ and chlorohydrocarbons and alkane and alkenes as further by-products. In a preferred embodiment, the dimethyldichlorosilane to be purified already contains chlorohydrocarbons in an amount =such that the H-silanes are converted virtually completely into the corresponding chloro-silanes by treatment with metallic palladium or platinum as catalysts.

The by-products of the direct synthesis are described, for example, in W. Noll, Chemistry and Technology of Silicones, Academic Press, Inc., Orlando, Florida, 1968, chapter 2.2, and A. Hunyar, Chemie der Silikone (Chemistry of the Silicones), Verlag Technik, Berlin 1952, pages 92 to 94.

The concentration of EtHSiCl$_2$ is usually 300 to 5000 ppm; however, the mixtures from the methylchlorosilane synthesis to be purified can also contain higher or lower concentrations of EtHSiCl$_2$.

For reasons of stoichiometry, at least one chlorine atom from the chlorohydrocarbons must be present per hydrogen atom for complete removal of the H-silanes. If the product mixtures from the methylchlorosilane synthesis to be purified do not contain the amount of chlorohydrocarbons necessary for complete removal of the H-silanes, further chlorohydrocarbons can be added to the reaction mixture.

Chlorohydrocarbons which are particularly suitable for the process according to the invention are saturated chlorohydrocarbons which contain at least two chlorine atoms on the same carbon atom, in particular a trichloromethyl group; ethylenically unsaturated chlorohydrocarbons which contain at least one chlorine atom on an unsaturated carbon atom or in the allyl position; and aromatic chlorohydrocarbons which contain at least one chlorine atom in a benzyl position.

Preferred chlorohydrocarbons contain 1 to 18, in particular 1 to 10, carbon atoms.

Chlorohydrocarbons which have boiling points which differ, like the boiling points of the reaction products of these chlorohydrocarbons, by at least 8° C. from the boiling point of Me$_2$SiCl$_2$ are preferred. Carbon tetrachloride and, in particular benzotrichloride (C$_6$H$_5$CCl$_3$) and, allyl chloride are particularly preferably employed.

The process according to the invention is preferably carried out under an inert gas atmosphere, such as under a nitrogen, argon or helium atmosphere, in particular under a nitrogen or argon atmosphere.

The process according to the invention is preferably carried out at a temperature of 20° to 150° C. under the pressure of the surrounding atmosphere. However, higher or lower temperatures and pressures can also be used.

Inert organic solvents, such as toluene, xylene or octane, can be used in the process according to the invention, although their co-use is not preferred.

The catalyst used according to the invention can be employed in the liquid phase or in the gas phase.

The process according to the invention can be carried out batchwise, semi-continuously or continuously. The continuous process is preferred.

In the continuous procedure, the residence time of the EtSiHCl$_2$ in a preferred embodiment is 0.5 to 60 seconds, depending on the starting concentration of the EtSiHCl$_2$, since short contact times in processes carried out continuously lead to high space/time yields.

In the following examples, unless stated otherwise, (a) all amounts are based on weight; (b) all pressures are 0.10 MPa (absolute) and (c) all temperatures are 20° C.

Abbreviations used are, Me: methyl radical and Et: ethyl radical.

EXAMPLES 1 to 6

Examples 1 to 6 shown in Table I are not according to the invention.

EXAMPLE 7

According to the invention, the number of grams indicated in Table I of dry catalyst and 30 g (0.3 mol) of methyldichlorosilane were added, under argon, to a three-necked flask fitted with a thermometer, dropping funnel and in intensive reflux condenser fitted with an inert gas connection. 25 g (0.3 mol) of allyl chloride were slowly added to this mixture via the dropping funnel, while stirring with a magnetic stirrer, and the reaction mixture was heated at 40° C. for 1 hour. A sample was taken and analyzed by means of 1H-NMR.

TABLE 1

| Example | Catalyst | No. of Grams | $^1$H-NMR MeHSiCl$_2$:MeSiCl$_3$ | | Results |
| --- | --- | --- | --- | --- | --- |
| 1 | Cu/C*) | 0.5 | 100 | 0 | no reaction |
| 2 | Ru/C**) | 0.5 | 96.5 | 3.5 | slight evolution of gas |
| 3 | Ni/C***) | 0.5 | 100 | 0 | no reaction |
| 4 | Active Charcoal | 0.5 | 100 | 0 | no reaction |
| 5 | FeCl$_3$ | 0.5 | 100 | 0 | no reaction |
| 6 | CuCl$_2$ | 0.5 | 100 | 0 | no reaction |
| 7 | Pd/C****) | 0.5 | 0 | 100 | exothermic reaction, evolu- |

TABLE 1-continued

| Example | Catalyst | No. of Grams | $^1$H-NMR MeHSiCl$_2$:MeSiCl$_3$ | Results |
|---|---|---|---|---|
| | | | | tion of gas |

*)5% copper-on graphite, from Johnson Matthey
**)5% ruthenium-on-charcoal, from Janssen Chimica
***)75% nickel-on-graphite, from Johnson Matthey
***)5% palladium-on-active charcoal, from Strem Chemicals Inc.

EXAMPLES 8 TO 10

Examples 8 to 10 in Table II, were conducted according to the invention.

0.5 g of dry palladium-on-active charcoal (5% of palladium, 95% of active charcoal, from Strem Chemicals Inc.) and 35 g (0.3 mol) of methyldichlorosilane were added to a three-necked flask fitted with a thermometer, dropping funnel and intensive reflux condenser fitted with an inert gas connection and flushed with argon. As indicated in Table II, a specified number of grams of an organochloride compound were added dropwise to this mixture and the reaction mixture was heated at a determined degree for the time indicated. A sample was taken and analyzed by means of 1H-NMR.

TABLE II

| Example | Chlorohydrocarbon | No. of Grams | No. Hours | Temp. | HMeSiCl$_2$:MeSiCl$_3$ | |
|---|---|---|---|---|---|---|
| 8 | Allyl chloride | 25 | 1 | 40° | 0 | 100 |
| 9 | Carbon tetrachloride | 12 | 1 | 50° | 0 | 100 |
| 10 | Benzyl chloride | 39 | 1 | 60° | 87 | 13 |

EXAMPLES 11 TO 14

In Table III, Examples 11 and 12 were conducted according to the invention and Examples 13 and 14 were not according to the invention.

A determined number of grams of dry catalyst were initially introduced into an argon flushed three-necked flask fitted with a thermometer, dropping funnel and intensive reflux condenser fitted with an inert gas connection. 50 g of dimethyldichlorosilane were added to the catalyst via the dropping funnel, while stirring with a magnetic stirrer. The Me$_2$SiCl$_2$ taken from a direct synthesis product stream which included as by-products alkanes, alkenes and chlorohydrocarbons which were not precisely identified, contained 520 ppm of ethyldichlorosilane as impurities. After a reaction time of 5 minutes at room temperature, a sample was taken and analyzed by means of gas chromatographs (GC). The reaction mixture was then heated at 60° C. for 5 minutes and likewise analyzed by means of GC.

TABLE III

| Example | Catalyst | No. of Grams | Temp. | EtHSiCl$_2$ |
|---|---|---|---|---|
| 11 | Pd/C*) | 0.5 | 20° | <1 ppm |
| 12 | Pd/C*) | 0.5 | 60° | <1 ppm |
| 13 | Active charcoal | 0.5 | 20° | 403 ppm |
| 14 | Active charcoal | 0.5 | 60° | 308 ppm |

*)5% palladium-on-active charcoal, from Strem Chemicals Inc.

EXAMPLE 15

According to the invention, 100 g of distilled Me$_2$SiCl$_2$ from a direct synthesis product stream were initially introduced in a nitrogen atmosphere into a three-necked flask fitted with a thermometer, dropping funnel and a mirrored glass column fitted with a distillation head. In addition to alkanes, alkenes and chlorohydrocarbons, this Me$_2$SiCl$_2$ contained 467 ppm of EtHSiCl$_2$ as impurities.

33 g of catalyst (granular active charcoal coated with 1.4% by weight of palladium) were introduced into the column.

The Me$_2$SiCl$_2$ was evaporated in the flask, while stirring, passed through the column, condensed in the distillation head and taken off. Me$_2$SiCl$_2$ was metered into the flask at the rate at which the distillate was removed from the system.

After a running time of 80 minutes, the reaction was discontinued and the distillate was analyzed by means of GC.

After 80 minutes, 280 g of distillate had collected (mass flow 210 g/hour); this corresponds to a residence time of about 1.9 seconds, based on gaseous Me$_2$SiCl$_2$, over the catalyst. The concentration of EtHSiCl$_2$ in the distillate was 3.8 ppm.

EXAMPLE 16

Example 15 was repeated, according to the invention, with the modification that 29 g of granular active charcoal (coated with 0.2% by weight of palladium) were introduced into the column as the catalyst.

After a running time of 110 minutes, the reaction was interrupted and the distillate was analyzed by means of GC. The amount of distillate was 415 g (mass flow 226 g/hour); this corresponds to a residence time of about 1.8 seconds, based on gaseous Me$_2$SiCl$_2$, over the catalyst. The concentration of EtHSiCl$_2$ in the distillate was 3.0 ppm.

EXAMPLES 17 TO 19 (ACCORDING TO THE INVENTION)

A 110-1-reactor, filled with 50 kg of catalyst (granular active charcoal coated with 2% by weight of palladium), was continuously charged at room temperature with a mixture of dimethyldichlorosilane and benzotrichloride. The dimethyldichlorosilane originated from a product stream from direct synthesis and, in addition to alkanes, alkenes and chlorohydrocarbons which were not identified precisely, contained ethyldichlorosilane. The analyses were made by GC before and after the reactor.

TABLE IV

| Example No. | Dimethyldochlorosilane [l/h] | Benzotrichloride [g/h] | EtHSiCl2 before reactor [ppm] | EtHSiCl2 after reactor [ppm] |
|---|---|---|---|---|
| 17 | 500 | 200 | 74 | 9 |
| 18 | 1000 | 275 | 75 | 12 |
| 19 | 1500 | 275 | 85 | 24 |

What is claimed is:

1. A process for the removal of silanes, containing hydrogen atoms bonded directly to silicon, from product mixtures obtained during methylchlorosilane synthesis, wherein the silanes, containing hydrogen atoms bonded directly to silicon, are reacted with chlorohydrocarbons in the presence of palladium or platinum as catalysts to give the corresponding chlorosilanes.

2. The process as claimed in claim 1, wherein EtSiHCl$_2$ is removed.

3. The process as claimed in claim 1, wherein the chlorohydrocarbons are selected from the group consisting of:
a. saturated hydrocarbons having at least one trichloromethyl group,
b. ethylenically unsaturated chlorohydrocarbons having at least one chlorine atom on an unsaturated carbon atom or in the allyl position,
c. aromatic chlorohydrocarbons having at least one chlorine atom in the benzyl position,
and mixtures thereof.

4. The process as claimed in claim 3, wherein allyl chloride is employed.

5. The process as claimed in claim 3, wherein the methylchlorosilane product to be purified contains an adequate amount of chlorohydrocarbons for virtually complete reaction of the silanes containing hydrogen atoms bonded directly to silicon.

6. The process as claimed in claim 3, wherein benzotrichloride is employed.

* * * * *